United States Patent
Asberg et al.

(10) Patent No.: US 7,507,584 B2
(45) Date of Patent: Mar. 24, 2009

(54) METHOD FOR THE DIAGNOSIS OF CHRONIC STRESS AND RELATED DISORDERS

(75) Inventors: Marie Asberg, Stockholm (SE); Ake Nygren, Stockholm (SE); Rolf Ekman, Mölndal (SE)

(73) Assignee: Randox Laboratories, Ltd. (GB)

( * ) Notice: Subject to any disclaimer, the term of this patent is extended or adjusted under 35 U.S.C. 154(b) by 0 days.

(21) Appl. No.: 11/587,297

(22) PCT Filed: Apr. 14, 2005

(86) PCT No.: PCT/GB2005/001417

§ 371 (c)(1),
(2), (4) Date: Jan. 31, 2008

(87) PCT Pub. No.: WO2005/103723

PCT Pub. Date: Nov. 3, 2005

(65) Prior Publication Data

US 2008/0153172 A1    Jun. 26, 2008

(30) Foreign Application Priority Data

Apr. 23, 2004   (GB) ................. 0409153.4

(51) Int. Cl.
*G01N 33/00* (2006.01)
*G01N 33/48* (2006.01)
(52) U.S. Cl. .................. 436/86; 436/63; 436/87
(58) Field of Classification Search ........... 436/63, 436/86, 87
See application file for complete search history.

(56) References Cited

U.S. PATENT DOCUMENTS

| 5,879,902 A | 3/1999 | Roberge et al. |
| 6,653,135 B1 | 11/2003 | Bradley |
| 7,288,374 B2 * | 10/2007 | Pincemail et al. ........ 435/6 |

FOREIGN PATENT DOCUMENTS

WO      WO 03/069310      8/2003

OTHER PUBLICATIONS

Ohlson et al. (abstract) Psychotherapy and Psychosomatics, vol. 70, No. 5, Sep.-Oct. 2001, pp. 268-275.*
Giannopoulos et al. "Effect of Inflammation, Smoking and Stress on Gingival Crevicular Fluid Cytokine Level", Database Medline, US National Library of Medicine, XP002340159, (2003).
Porcu et al., "Reversal of Angiogenic Growth Factor Upregulation by Revascularization of Lower Limb Ischemia", Circulation, vol. 105, pp. 67-72 (2002).
Shweiki et al., "Induction of Vasular Endothelial Growth Factor Expression by Hypoxia and by Glucose Deficinecy in Multicell Spheroids: Implications for Tumor Angiogenesis", Proc. Natl. Acad. Sci., vol. 92, pp. 762-772 (1995).
Fabel et al., "VEGF is Necessary for Exercise-Induced Adult Hippocampal Neurogenesis", European Journal of Neuroscience, vol. 18, pp. 2803-2812 (2003).
Lutgendorf et al., "Vascular Endothelial Growth Factor and Social Support in Patients with Ovarian Carcinoma", Cancer, vol. 95, pp. 808-815 (2002).

* cited by examiner

*Primary Examiner*—Maureen M Wallenhorst
(74) *Attorney, Agent, or Firm*—McDonnell Boehnen Hulbert & Berghoff LLP

(57) ABSTRACT

Methods for diagnosing chronic stress in patients by first determining the level of one or more analytes in a patient sample and establishing the significance of the one or more analyte levels.

7 Claims, No Drawings

METHOD FOR THE DIAGNOSIS OF CHRONIC STRESS AND RELATED DISORDERS

FIELD OF INVENTION

The present invention relates to the diagnosis of chronic stress and related disorders.

BACKGROUND OF THE INVENTION

Chronic stress is involved in the development of several different diseases in the nervous, endocrine and immune systems. Stressors of various types, e.g. psychological, physical and biological, abound. Sustained stress related to work appears to be an increasingly important factor for the development of both physical and mental illness (see Tennant, Journal of Psychosomatic Research, 2001, 51(5), 697-704; and Vahtera, Lancet, 1997, 350 (9085), 1124-1128).

In Sweden alone, public expenditure for sick-leave has more than doubled over a few years, and, in 2003, the number of persons on long-term sick leave (i.e. more than 30 days) had increased to an all-time high. Much of this dramatic increase appears to be due to stress-related affective illness. The question remains whether mild or moderate stress-induced depression should be seen as a purely psychological disorder, or whether the characteristic syndrome of fatigue, tension and dysphoria has physical connotations.

The physiological pathways that lead from prolonged stress to exhaustion and depression are likely to involve both the hypothalamus-pituitary-adrenal axis and other endocrine systems, as well as the immune system (see Folkow et al, Acta Physiologica Scandinavica, 1997, 161). The exact sequence of events in the brain-endocrine-immune, systems under chronic stress is not well known in humans, but recent progress in immunology has lead to increasing focus on the links between cytokines and depressive illnesses.

Cytokines are low molecular weight proteins or glycoproteins that were initially characterised as communication molecules of the immune system. They can be secreted by a number of different cell types and play a key role in the regulation of the immune system and the co-ordination of the host response to injury and infection. Cytokines produce their actions by binding to specific high-affinity cell surface receptors. The range of actions displayed by individual cytokines can be broad and diverse and is dependent on the receptor. Receptors can be soluble and can bind to the cytokine, in turn inhibiting the binding of the cytokine to the cell surface receptor, blocking its biological. Cytokines operate within a complex network and may act synergistically or antagonistically. They can influence the production of other cytokines from other cell types. Initially, it was thought that the cytokines were restricted to the immune system but it has since been demonstrated that they are also involved in signalling in the central nervous and endocrine systems.

In 1991, Smith formulated the macrophage theory of depression. This hypothesis proposed that excessive secretion of macrophage cytokines such as IL-1, TNFa and IFNg, were a cause of some cases of major depression. Both before and after the proposal of this theory, others have reported that when previously psychiatrically healthy individuals have been treated with exogenous cytokines they develop depressive-like symptoms. This has also been observed in patients being treated with cytokines such as IFNg, where 80% of patients reported fatigue from moderate to severe intensity. The same has been found with administration of certain cytokines to experimental animals. Many studies have measured the circulating levels of cytokines in relation to one or more specific stressors, but these studies have revealed conflicting results due to sample sizes being small and the use of different assays making results difficult to interpret. In vitro cytokine secretion by stimulation of the peripheral blood lymphocytes has also been studied in relation to stress and depression. These studies have almost exclusively focused on IL-6, IL-1, TNFa and IFNg. Again, the results have varied and no definite pattern has emerged.

Cytokines can be measured by either immunoassay or bioassay. Bioassays measure the functional activity of cytokines and require that some measure of biological activity be recorded. Bioassays can lack specificity as other cytokines present in the sample can give the same response in the assay or because the sample may contain inhibitors which block them. Also, if the cytokines have been proteolytically degraded they will not retain biological activity. Immunoassays are based on an antibody that recognises a small portion of the cytokine and therefore most are very specific for the cytokine being measured. It is possible for biologically inactive cytokines and proteolytically degraded cytokines to be measured. Until very recently most of the cytokine immunoassay measurements have been performed using individual ELISAs.

At present, no reliable markers of chronic stress and related disorders (e.g. stress-related depression) have been identified.

SUMMARY OF THE INVENTION

The present invention is based on the discovery of a number of potential markers of chronic stress, namely VEGF, IL-8, MCP1, EGF and TSH.

Accordingly, a first aspect of the invention is a method of diagnosis of chronic stress in a patient, which comprises:
(a) determining the level of each of one or more analytes in the patient, wherein the one or more analytes are selected from VEGF, IL-8, MCP1, EGF and TSH; and
(b) establishing the significance of the or each level.

Preferably, the or each level is determined using a sample (e.g. a blood sample) taken from the patient.

DESCRIPTION OF THE INVENTION

The term "chronic stress" as used herein refers to chronic stress as diagnosed according to the Hospital Anxiety and Depression Scale of Snaith and Zigmond, Br. Med. J, Clin. Res. Ed., 1986, 292, 6516, 344.

Elevated levels of VEGF, MCP1, IL-8 and EGF, or reduced levels of TSH are believed to be indicative of chronic stress. Without wishing to be bound by theory, it is believed that one or more of the following are indicative of chronic stress: VEGF levels of at least about 25 pg/ml, EGF levels of at least about 70 pg/ml, IL-8 levels of at least about 3 pg/ml (particularly in men) and MCP1 levels of at least about 220 pg/ml. It will be appreciated that the benchmark levels may vary somewhat between patients and depend on factors such as the age, general health, weight, sex and diet of the patient in question. In particular, the sex of the patient may be a crucial factor since analyte levels generally differ in men and women. A method of the invention preferably comprises determining a plurality of analytes, the analytes preferably including VEGF, MCP1 and EGF.

It is envisaged that a method of the invention may also be used for the diagnosis of disorders related to chronic stress, for example stress-related depression. In this case, the control may be a person not suffering from a major depressive disorder. The term "major depressive disorder" as defined herein refers to a major depressive disorder as diagnosed according to the Diagnostic and Statistical Manual of the American Psychiatric Association, 4th Edition.

The levels of the or each analyte may be determined using any suitable method known in the art. A preferred system is the "Evidence" immunoassay analyser (Randox Laboratories Ltd). The Evidence system is a fully automated immunoassay analyser based on a protein biochip array technology and allows for the simultaneous quantification of a plurality of analytes. For example, the Evidence cytokine and growth factor panel can determine the presence of up to twelve analytes in a single sample.

The invention will now be illustrated by way of example only.

Subjects

Patients on Long Term Sick Leave for Affective Disorder 287 patients (77 men and 210 women) on sick-leave (for more than three months) for any affective or stress-related mental disorder (depression, anxiety disorder, stress disorder, burnout, exhaustion), were recruited. All patients were ambulatory and none had received in-patient care for their current illness. They were diagnosed by specially trained physicians for chronic stress according to the Hospital Anxiety and Depression scale of Snaith and Zigmond. They were also diagnosed for stress-related depression according to the Diagnostic and Statistical Manual of the American Psychiatric Association, 4th Edition ("DSM-IV", 1994), using the Structured Clinical Interview for DSM-IV ("SCID-I,", 1997). 82% of patients fulfilled DSM-IV criteria for Major Depressive Disorder at some time during their current illness episode. Likely eliciting factors could be identified for all subjects.

Health Care Personnel with Occupational Stress

A group of women experiencing work stress. Of the employees who replied to the and who scored above the 75th percentile on the Oldenburg Burnout Inventory ("OLBI", which measures the degree of professional burnout; see Demerouti et al, Journal of Applied Psychology, 2001, 86(3), 499-512) were invited to participate in a randomised controlled study of the possible beneficial effect of a series of structured group discussions with colleagues. Those who were randomised to active treatment were asked to leave blood samples. The resulting group consisted of 45 women, ranging in age from 39 to 62 years, the mean age being 52.8±52 years.

Healthy Control Workers

The reference group comprised 187 individuals (104 men and 83 women, having a mean age of 36±7.5 yrs, and a range of 22-61 years), recruited. The subjects were all full-time workers, 34% were managers and 54% project leaders. Two women were pregnant at the time of the physiological examination.

Methods

Venous blood was drawn and immediately centrifuged, plasma was separated and stored in aliquots at $-20°$ C. or below until analysed.

Among the various cytokines and growth factors analysed were: interleukin 8 (IL8), monocyte chemotactic protein-1 (MCP1), epidermal growth factor (EGF) and vascular endothelial growth factor (VEGF). Furthermore, thyroid stimulating hormone (TSH) and testosterone were included in the panel analysed using the "Evidence" immunoassay system (Randox Laboratories Ltd). The assays were done on coded plasma samples by investigators who were unaware of subject category.

Results

Means and standard deviations of the 17 markers in men and women, on sick leave for stress-induced depression, still working but experiencing high levels of occupational stress, and apparently healthy controls, are shown in Tables 1 and 2.

In the women, there were very large differences between the three subject groups for MCP1, EGF and VEGF. MCP1 levels were more than twice as high in the sick leave group compared to the healthy controls, with the occupational stress group in between. VEGF levels were three times as high in the sick leave group, and EGF levels were more than twice as high, compared to the healthy group, once more with the occupational stress group in between. The sick leave group also had significantly lower levels of prolactin and TSH.

In the men, it was not possible to gain access to an occupational stress group, and the comparisons are therefore between men on sick leave and apparently healthy controls. Among the men, IL-8 levels were significantly increased in the sick leave group, while testosterone levels were decreased. As in the women, the greatest differences were shown for MCP1, EGF and VEGF, which were two to three times as high in the sick leave group.

Since there were weak but significant correlations between some of the markers and age, and the mean age differed significantly between the groups (women one-way ANOVA F=59.09 df=2, 338 P=0.000; men T=8.87 df=174 p=0.000), the data was controlled for age in an analysis of covariance. This resulted in one additional significant difference for the women, namely in testosterone, which was higher in the sick leave group. Among men, when controlling for age, the significant effects of testosterone found by using a T-test disappeared in the analysis of covariance. Thus, four markers, IL8, MCP1, VEGF and EGF, remained significant in the men.

In order to examine the usefulness of these markers for screening and diagnostic purposes, a receiver operating characteristic (ROC) curve analysis (according to Metz, Semin Nucl Med, 1978, 8(4), 283-98) was performed. As Table 3 shows, the best sensitivity and specificity was obtained for MCP1, VEGF, and EGF.

The relative value of MCP1, EGF, and VEGF, as risk factors for classification as ill or healthy was tested for women and men. The results are shown in Table 4, and indicate that each of these markers independently associates with a significantly increased risk for being classified as ill.

TABLE 1

| Marker | Sick leave | | Occupational stress | | Healthy | | ANOVA | | | Significant pairwise comparisons |
|---|---|---|---|---|---|---|---|---|---|---|
| | M | SD | M | SD | M | SD | F | Df | P | |
| IL8 | 5.4 | 10.8 | 3.3 | 2.9 | 3.1 | 1.3 | 2.98 | 2,338 | .052 | |
| MCP1 | 348.4 | 126.7 | 217.8 | 92.6 | 160.2 | 85.7 | 97.82 | 2,338 | .000* | 1-2, 1-3, 2-3 |

TABLE 1-continued

|  | Sick leave | | Occupational stress | | Healthy | | ANOVA | | | Significant pairwise |
|---|---|---|---|---|---|---|---|---|---|---|
| Marker | M | SD | M | SD | M | SD | F | Df | P | comparisons |
| EGF | 117.0 | 77.2 | 70.6 | 53.0 | 29.4 | 47.5 | 56.16 | 2,338 | .000* | 1-2, 1-3, 2-3 |
| VEGF | 30.9 | 22.7 | 18.4 | 15.4 | 10.3 | 7.1 | 41.24 | 2,338 | .000* | 1-2, 1-3 |
| TSH | 1.8 | 1.0 | 2.4 | 1.6 | 2.4 | 1.2 | 11.11 | 2,342 | .000* | 1-3 |
| Testosterone | 4.1 | 1.5 | 4.0 | 1.8 | 3.5 | 1.4 | 5.39 | 2,330 | .005 | |

*Significant at the .05 level
Table 1: Biochemical markers in women experiencing different levels of stress, patients on long term sick leave for affective disorders (Sick leave; 1), health care personnel at risk for professional burnout (Burnout; 2) and healthy controls (Healthy; 3) employed in an IT company. Means (M), standard deviations (SD), and one-way ANOVA:s: F-ratios (F), degrees of freedom (Df) and P-value (P), (significance corrected according to Bonferroni's method), and post-hoc analysis according to Scheffe's method.

TABLE 2

|  | Sick leave | | Healthy | | | | |
|---|---|---|---|---|---|---|---|
| Marker | M | SD | M | SD | T | Df | P |
| IL8 | 4.9 | 5.0 | 2.8 | 0.9 | 4.10 | 178 | .000* |
| MCP1 | 404.9 | 148.6 | 176.3 | 61.4 | 14.10 | 178 | .000* |
| EGF | 119.5 | 76.5 | 26.0 | 41.5 | 10.51 | 178 | .000* |
| VEGF | 38.7 | 29.5 | 11.2 | 8.5 | 8.98 | 178 | .000* |
| TSH | 1.8 | 1.3 | 2.2 | 0.9 | 2.62 | 174 | .010 |
| Testosterone | 19.6 | 7.8 | 23.3 | 6.2 | 3.44 | 167 | .001* |

*Significant at the .05 level
Table 2: Biochemical markers in men experiencing different levels of stress, patients on long term sick leave for affective disorders (Sick leave), and healthy controls (Healthy) employed in an IT company. Means (M), standard deviations (SD), and independent T-tests (significance corrected according to Bonferroni's method).

TABLE 3

| Gender | Marker | Area | Cut-off | Sensitivity | Specificity |
|---|---|---|---|---|---|
| Women | MCP1 | 0.886 | 243.00 | 0.85 | 0.92 |
| | VEGF | 0.805 | 7.80 | 0.78 | 0.85 |
| | EGF | 0.798 | 68.00 | 0.69 | 1.00 |
| | TSH | 0.624 | 1.80 | 0.58 | 0.69 |
| | Testosterone | 0.618 | 3.73 | 0.63 | 0.65 |
| Men | MCP1 | 0.869 | 226.00 | 0.92 | 0.82 |
| | EGF | 0.859 | 30.00 | 0.92 | 0.80 |
| | VEGF | 0.817 | 7.80 | 0.78 | 0.85 |
| | IL8 | 0.801 | 3.00 | 0.87 | 0.72 |

Table 3: Optimal cut-off, area under the ROC-curve (Area), and diagnostic sensitivity and specificity of statistically significant biochemical markers in women and men.

TABLE 4

| Gender | Marker | Beta | Wald | P | OR | 95% CI |
|---|---|---|---|---|---|---|
| Women | MCP1 | 3.55 | 52.17 | 0.000 | 34.85 | 13.30-91.35 |
| | EGF | 2.12 | 18.02 | 0.000 | 8.35 | 3.13-22.25 |
| | VEGF | 2.08 | 18.99 | 0.000 | 8.02 | 3.14-20.44 |
| Men | MCP1 | 3.64 | 26.96 | 0.000 | 37.97 | 9.62-149.83 |
| | EGF | 3.56 | 25.39 | 0.000 | 35.09 | 8.79-140.05 |
| | VEGF | 2.18 | 11.64 | 0.001 | 8.85 | 2.53-30.95 |

Table 4: Relative risks of being classified as ill, using the established cut-off points of MCP1, EGF and VEGF (Table 3). Multiple logistic regression analyses in men and women. OR signifies Observed risk, with 95 per cent confidence interval (95% CI)

The invention claimed is:

1. A method of diagnosis of chronic stress in a patient, which comprises:
    (a) determining the level of each of analytes vascular endothelial growth factor (VEGF), monocyte chemotactic protein-1 (MCP1) and epidermal growth factor (EGF) in a sample taken from the patient; and
    (b) establishing the significance of each analyte level by comparing each analyte level to the same analyte levels measured in a healthy control sample, and diagnosing chronic stress in the patient when each analyte level is elevated relative to the analyte levels measured in the healthy control sample.

2. A method according to claim 1, wherein the sample is a blood sample.

3. A method of diagnosis of chronic stress in a patient, which comprises:
    (a) determining the level of each of analytes vascular endothelial growth factor (VEGF), monocyte chemotactic protein-1 (MCP1) and epidermal growth factor (EGF) in a sample taken from the patient; and
    (b) establishing the significance of each analyte level by comparing each analyte level with those of a control sample, wherein the control sample is from a person who is not suffering from a major depressive disorder and diagnosing chronic stress in the patient when each analyte level is elevated relative to the analyte levels in the control sample.

4. A method according to claim 1 or 2 wherein step (a) additional comprises determining the level of interluken-8 (IL-8).

5. A method according to claim 4 wherein step (a) additional comprises determining the level of thyroid stimulating hormone (TSH).

6. A method according to claim 1 or 2 wherein step (a) additional comprises determining the level of thyroid stimulating hormone (TSH).

7. A method according to claim 3, wherein the patient sample is a blood sample.

* * * * *